United States Patent [19]
Maarse

[11] Patent Number: 5,741,309
[45] Date of Patent: Apr. 21, 1998

[54] BREAK ALGORITHM FOR PR+PVARP BLOCK

[75] Inventor: Albert Maarse, SX Aalsmeer, Netherlands

[73] Assignee: Cardiac Pacemakers, Inc., St. Paul, Minn.

[21] Appl. No.: 802,543

[22] Filed: Feb. 18, 1997

[51] Int. Cl.⁶ ................................................ A61N 1/362
[52] U.S. Cl. ................................................ 607/9
[58] Field of Search ................................................ 607/9

[56] References Cited

U.S. PATENT DOCUMENTS

| | | | |
|---|---|---|---|
| 4,920,965 | 5/1990 | Funke et al. | 607/9 |
| 5,395,396 | 3/1995 | Lindgren et al. | 607/9 |
| 5,527,347 | 6/1996 | Shelton et al. | 607/9 |
| 5,609,610 | 3/1997 | Nappholz | 607/9 |
| 5,643,326 | 7/1997 | Weiner et al. | 607/9 |

Primary Examiner—William E. Kamm
Attorney, Agent, or Firm—Haugen & Nikolai, P.A.

[57] ABSTRACT

A method of pacing a congestive heart failure (CHF) patient's heart using a pacemaker typically capable of bradycardia dual chamber pacing. The method includes an algorithm for resetting the timing interval of the microprocessor based controller of the pacemaker for stimulating the ventricles after a predetermined AV delay, when a legitimate signal associated with atrial events is blocked by a preprogrammed Post Ventricular Atrial Refractory Period (PVARP).

11 Claims, 5 Drawing Sheets

BREAK ALGORITHM FOR PR+PVARP BLOCK

BACKGROUND OF THE INVENTION

I. Field of the Invention

This invention relates generally to a method of pacing a patient's heart and more particularly to a method of pacing a congestive heart failure (CHF) patient's heart using a pacemaker typically capable of dual chamber bradycardia pacing. The method includes an algorithm for resetting the preset ventricular pacing interval when a legitimate signal associated with atrial depolarization events is blocked by a Post Ventricular Atrial Refractory Period (PVARP) preprogrammed into the dual chamber pacer.

II. Discussion of the Related Art

Typically, patients suffering from a higher degree of AV-block are implanted with a pacemaker suited for pacing the ventricle in the absence of an intrinsic rhythm. This sort of pacemaker is used, for example, in normal bradycardia dual chamber pacing. The purpose of pacing the heart of a patient who suffers from normal bradycardia is to make sure that heart beats are properly timed and not omitted. Intrinsic rhythm is favorable over paced rhythm for both hemodynamic and economic reasons. If the pacemaker is set to pace only on demand during periods when an intrinsic beat has been omitted, there is less current drain, thereby prolonging the useful life of the implanted pacemaker.

Patients' suffering from congestive heart failure (CHF) either do not exhibit heart block at all or often only suffer from a first degree AV-block or a slightly prolonged delay interval between the depolarization of the atrium and the depolarization of the ventricle. Although it is not currently common to pace the heart of a CHF patient, recent research has shown that coordinated pacing can improve hemodynamic performance of a sick heart. However, any pacing should be performed continuously. Pacing the heart of a patient suffering from CHF requires continuous pacing in order to improve the contraction pattern, even though intrinsic beats would occur slightly later if there were no pacing. When pacing a patient suffering from CHF, it is highly undesirable to omit pacing when it is supposed to occur.

Under certain conditions, when pacing the heart of a CHF patient, utilizing a dual chamber pacemaker suitable for pacing the ventricle in the absence of an intrinsic rhythm, a situation may result where pacing of the ventricle is interrupted or does not occur where it would be expected. For example, in dual chamber bradycardia pacing, depolarization in the atrium and ventricles is sensed and the pacing interval of the ventricle is restrained by two periods, the Post Ventricular Atrial Refractory Period (PVARP) and the Upper Rate Interval (URI). The URI corresponds with a preset Upper Rate Limit (URL). Typically, the AV-delay plus the PVARP must be less than the preset URI. In bradycardia patients, if the intrinsic rate of pacing the atrium and ventricles rises slightly above the URI, a pseudo-Wenckebach block occurs, a ventricular stimulus is dropped and the Wenckebach cycle repeats. When the intrinsic rate drops below the programmed URL, then 1:1 ventricular pacing is restored.

In contrast, when pacing a CHF patient, an omission of pacing the ventricle is undesirable. Hence, it is very important in dealing with CHF patients that the programmed AV-delay+PVARP be less than the URI to avoid a block in the ventricle pacing. Often times this is not a problem since in the case of CHF patients, a very short AV-delay will be preprogrammed. However, if the intrinsic rate of pacing exceeds the preset Upper Rate Limit (URL) even for a moment, the intrinsic conduction will take over when a P-wave is masked by the PVARP and the ventricular stimulus is omitted. This causes the pacer to cease stimulation to the ventricles until a P-wave falls outside the PVARP. Unless ectopic activity occurs, this means that the sinus rate has to drop so much that the PP interval gets greater than PR+PVARP. This situation is known as PR+PVARP block. Hence, a need exists for a method of dual chamber pacing the heart of a CHF patient that breaks an occurring PR+PVARP block to thus insure that the CHF patient will continue to have his or her heart paced at uniform, fixed intervals. The present invention addresses this need.

SUMMARY OF THE INVENTION

The purpose of the present invention is to provide a method of pacing a heart of a CHF patient which includes an algorithm executable in the pacer's microprocessor for detecting the occurrence of PR+PVARP block and for discontinuing or breaking a PR+PVARP block which may be created when the PVARP value, pre-programmed into the dual chamber pacer, masks a legitimate P-wave and atrial events are ignored. A legitimate P-wave refers to a signal or wave that corresponds to an atrial depolarization. The preferred method of pacing the heart of a CHF patient includes sensing atrial activity and subsequently pacing the corresponding ventricles, where typically a very short AV-delay is preset. Without additionally limiting the pacing of the ventricles, a retrograde conduction from the ventricles to the atrium may create an incorrect determination by the pacemaker that an atrial event has occurred, thereby causing a pacemaker mediated tachycardia (PMT).

Oftentimes, to eliminate PMT's, the physician preprograms the pacemaker, setting the PVARP (wherein all signals from the atria are treated as noise) to a period normally long enough to block out a retrograde conduction, for example, 300 milliseconds. The physician also preprograms the fastest time the pacer is allowed to pace, hereinafter referred to as the upper rate limit or URL. At times, the heart rate will exceed the upper rate which will terminate pacing of the ventricles by the pacemaker. Pacing of the ventricles by the pacemaker will not resume until the rate is less than PR+PVARP. A naturally occurring premature ventricular contraction or PVC may realign the PVARP with the atrial events, thereby allowing ventricular pacing to resume, but one cannot depend on such an event happening. Therefore, the preset PVARP must be less than the URI–PR, but PVARP must also be greater than the retrograde conduction time.

In order to recognize the PR+PVARP block, the sinus rate, atrial events, ventricular events and PVARP are all monitored simultaneously. When the sinus rate is less than the URL and an atrial event is sensed during the PVARP, the PR+PVARP block can be recognized. After a predetermined number of cycles where an atrial event is sensed during a PVARP, the pacemaker is programmed to ignore or shorten the PVARP and/or URI, pacing the ventricles after the next sensed AV-event thereby breaking the PR+PVARP block. The PR+PVARP block may also be broken by shortening the PVARP and/or URI for a predetermined number of cardiac cycles before resuming the normal PVARP. Further, the PR+PVARP block may be broken by shortening or ignoring the PVARP until the rate of pacing the ventricles falls below the URL. In each of these situations, normal pacing then continues until the heart rate once again exceeds the URI. The break algorithm is then repeated.

OBJECTS

It is accordingly a principal object of the present invention to provide a method of multiple chamber pacing the heart of a patient suffering from CHF, wherein the method detects and eliminates a PR+PVARP block.

A further object of the present invention is to provide a method of pacing the ventricles of a patients heart a predetermined amount of time after a contraction of the atrium, while detecting and eliminating any resulting PR+PVARP block.

Another object of the present invention is to provide a method of dual chamber pacing that breaks a PR+PVARP block while reducing the likelihood of creating a PMT.

These and other objects, as well as these and other features and advantages of the present invention will become readily apparent to those skilled in the art from a review of the following detailed description of the preferred embodiment in conjunction with the accompanying drawings and claims and in which like numerals in the several views refer to corresponding parts.

DETAILED DESCRIPTION

Figure 1:
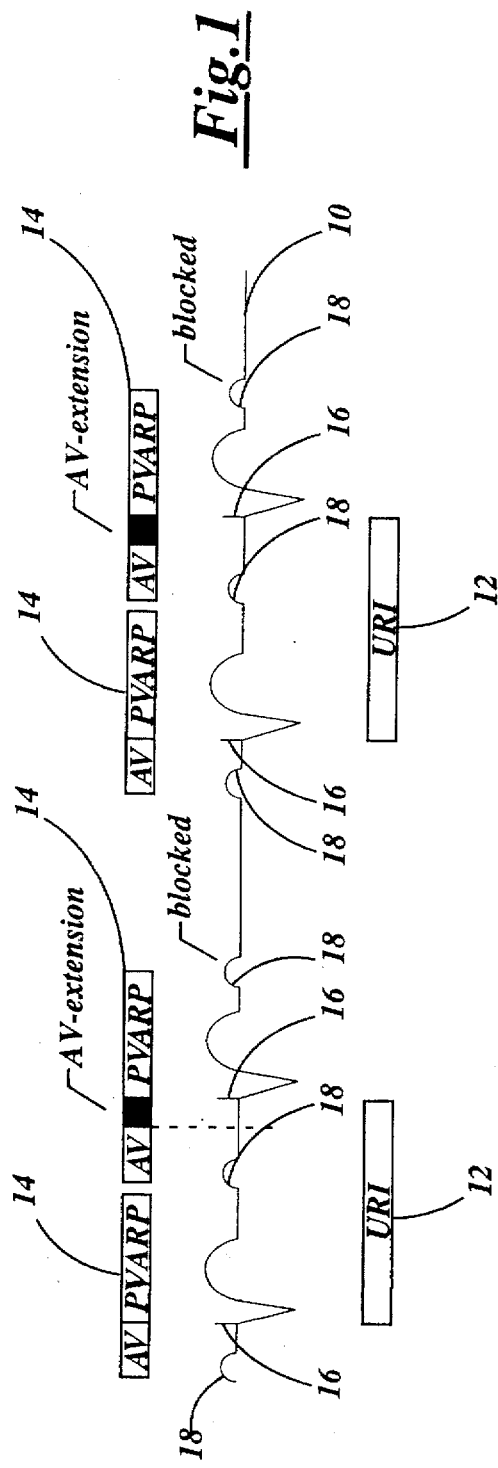
FIG. 1 is an ECG plot showing a heart wave in conjunction with preset AV, URI and PVARP timing intervals.

Referring first to FIGS. 1–3 and FIGS. 5–7, these figures illustrate sequentially a representative ECG wave form signal 10 over time, but with the T wave omitted. Overlaid on the plot are time intervals representing the preprogrammed URI and PVARP intervals of the pacemaker respectively identified by numerals 12 and 14, before, during and after a PR+PVARP block. Referring first to FIG. 1 there is shown generally the ECG wave 10 wherein a ventricle of the heart is being paced. The timing of the pacing stimulation spike is indicated by vertical line 16. The preceding atrial event is indicated by numeral 18.

Figure 2:
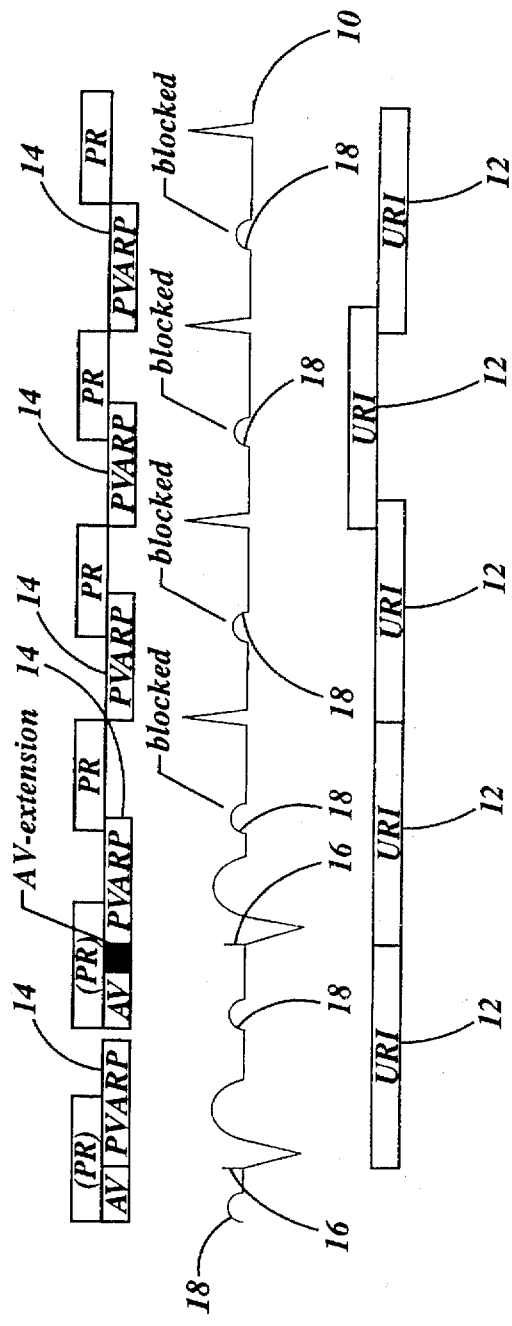
FIG. 2 is an ECG plot showing a heart wave in conjunction with the pacer's URI, PVARP, and PR intervals, wherein several of the atrial events are being blocked by the PVARP interval.

The pacemaker is preprogrammed to incorporate a PVARP and URI. These intervals, which are preset periods of time, are initiated after the ventricle has been stimulated or paced. As is well known, PVARP is a period of time established in the pacer circuitry when all sensed atrial events are ignored by the atrial sense amplifier. The URI is a minimal amount of time that can elapse between successive stimulations of the ventricle. As seen in FIG. 1, when the PVARP+AV delay is less than the URI, the period of time between atria depolarization and ventricular pacing must be extended; this extension interval is known as an AV-extension. The AV-extension, in turn, shifts the PVARP interval, which then blocks detection or sensing of the hearts naturally occurring atrial activity. As shown in FIG. 2, with CHF patients the pacemaker is not reset to the intrinsic activity of the atria, because the omission of the ventricular stimulus results in an intrinsically conducted ventricular cycle, which triggers another PVARP, which in turn will block the sensing of the next atrial activity, thereby creating the condition for the PR+PVARP block.

Figure 3:
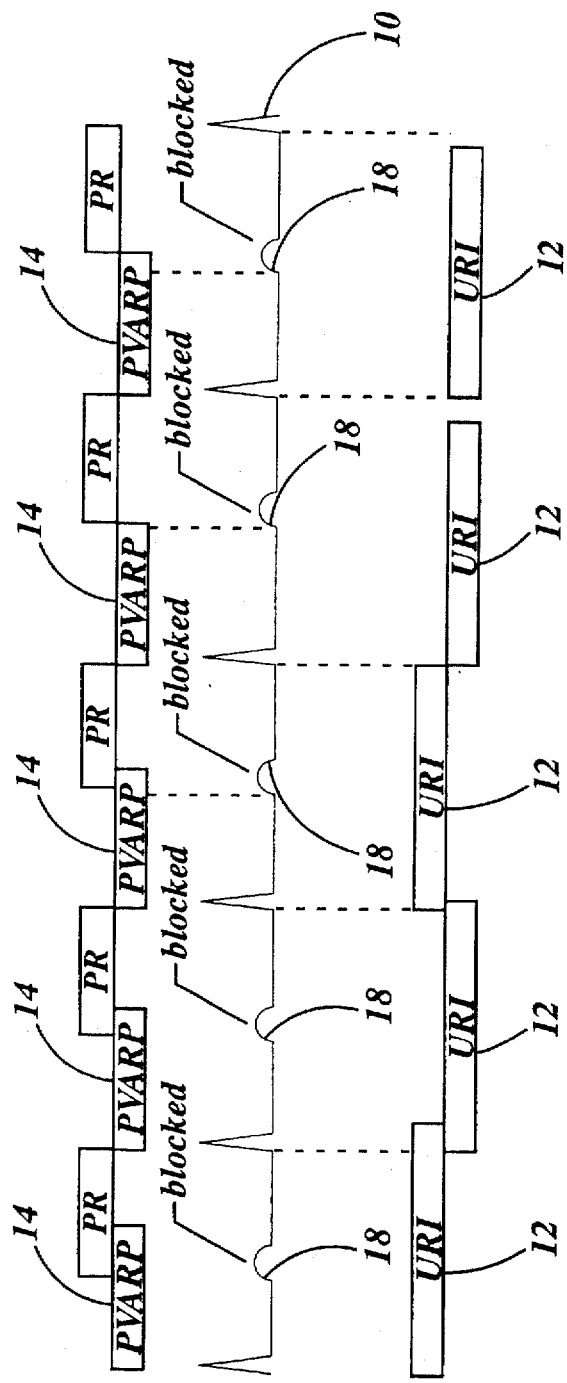
FIG. 3 is an ECG plot showing a heart wave in conjunction with the pacer's URI, PVARP, and PR intervals, wherein several of the atrial events are being blocked by the PVARP interval.

FIGS. 2 and 3 illustrate the resulting ECG waveform when the PVARP blocks the atrial activity, thereby causing the pacer to inhibit pacing of the ventricles until an atrial event is sensed. The PR interval or time between depolarization of the atrium and ventricle, is further indicated on these plots. As can be seen from FIG. 3, atrial events are blocked from the pacemakers sensing means when the combined PR-interval and PVARP are greater than the P—P interval, even when the heart rate interval is greater than the Upper Rate Interval. This situation is known as the PR+PVARP block, and can occur with heart rate intervals ranging from the URI to the sum of the PR interval and PVARP.

Figure 4:
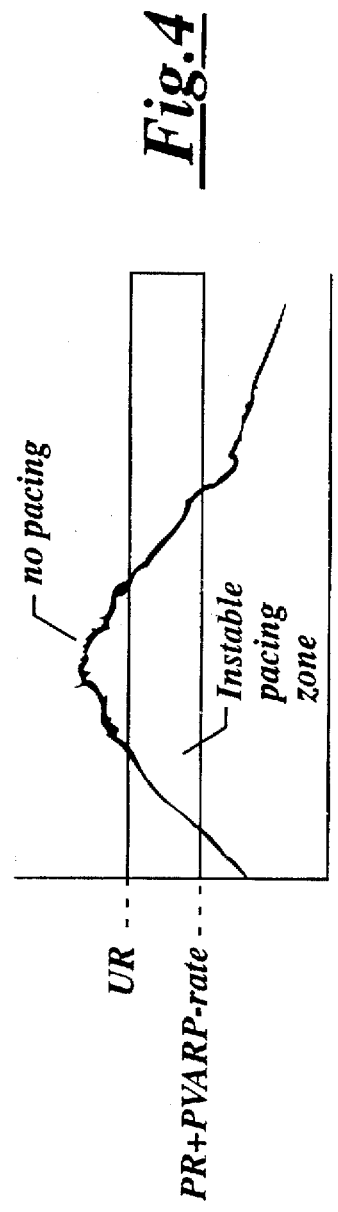
FIG. 4 is a graph showing the blocking hysteresis resulting when the upper rate limit is exceeded and, identifying the pacing zone where no pacing of the ventricles occurs until the heat rate falls below the PR+PVARP rate.

FIG. 4 is a graphical representation of heart rate over time showing the instable pacing zone and the resulting hysteresis effect if the heart rate exceeds the upper rate limit or maximum tracking rate of the URI. As seen in FIGS. 3 and 4 once the heart rate has exceeded the upper rate limit pacing will not restart until PR+PVARP becomes less than the PP interval.

Figure 5:
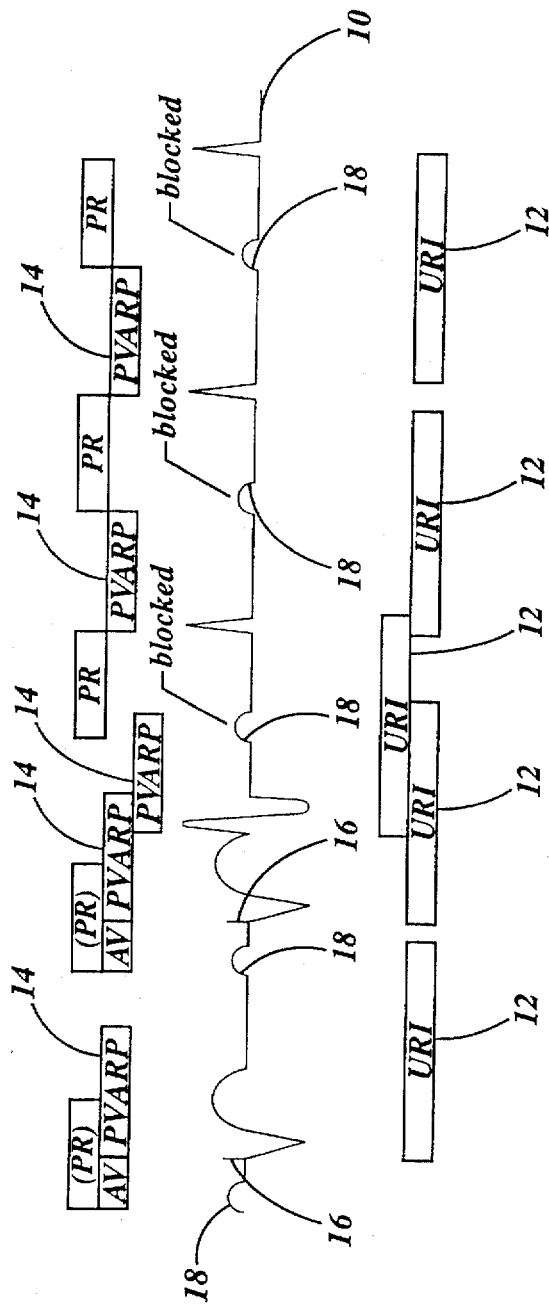
FIG. 5 is an ECG plot showing a heart wave in conjunction with the pacer's URI, PVARP, and PR intervals, wherein several of the atrial events are being blocked by the PVARP interval following an occurrence of a natural PVC.
Figure 6:
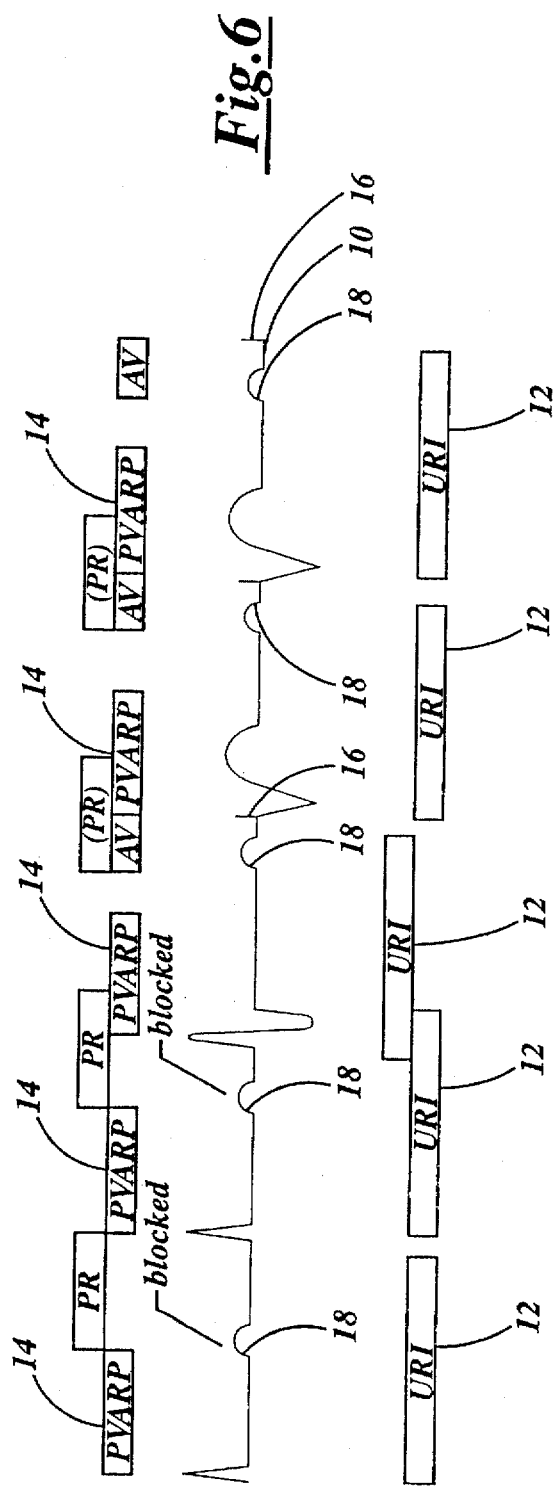
FIG. 6 is an ECG plot showing a heart wave in conjunction with the pacer's URI, PVARP, and PR intervals, wherein several of the atrial events are being blocked by the PVARP intervals prior to an occurrence of a natural PVC.

As seen in FIG. 5 pacing may naturally start once again when the PR+PVARP becomes less than the PP interval. FIG. 5 also shows that a PVC can realign the timing intervals of PVARP and AV-delay, thereby shifting the PVARP such that the atrial activity is blocked. FIG. 6 shows how a second PVC can further shift the PVARP interval, causing the atrial activity to once again be sensed and the ventricles paced.

Figure 7:
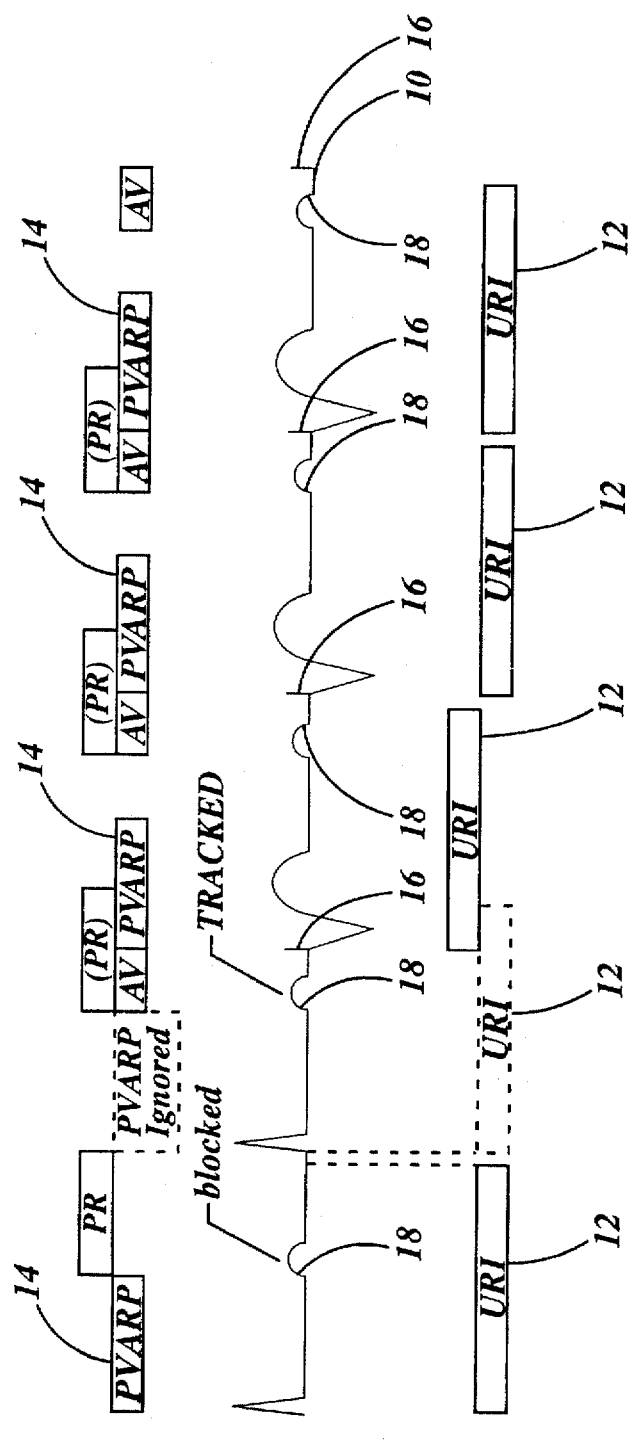
FIG. 7 is an ECG plot showing a heart wave in conjunction with the pacer's URI, PVARP and PR intervals, wherein the PR+PVARP block is eliminated and normal pacing resumes.

FIG. 7 further illustrates the solution to the PR+PVARP block problem that may occur when a dual chamber pacer is being used to pace a CHF patient. After a predetermined number of cycles wherein the atrial activity has been blocked, the pacemaker is programmed to ignore or shorten the PVARP and the URI such that once an atrial activity is sensed the pacemaker can again pace the ventricles. This then realigns the PVARP, URI and PR of the patient until such time as the heart rate exceeds the URL. The pacemaker may likewise be programmed to ignore or shorten the PVARP for a predetermined number of cardiac cycles. This likewise would realign the PVARP, URI, and PR of the patient. Similarly the pacemaker may be programmed to shorten or ignore the PVARP until a rate of pacing the corresponding ventricle falls below the URL.

Figure 8:
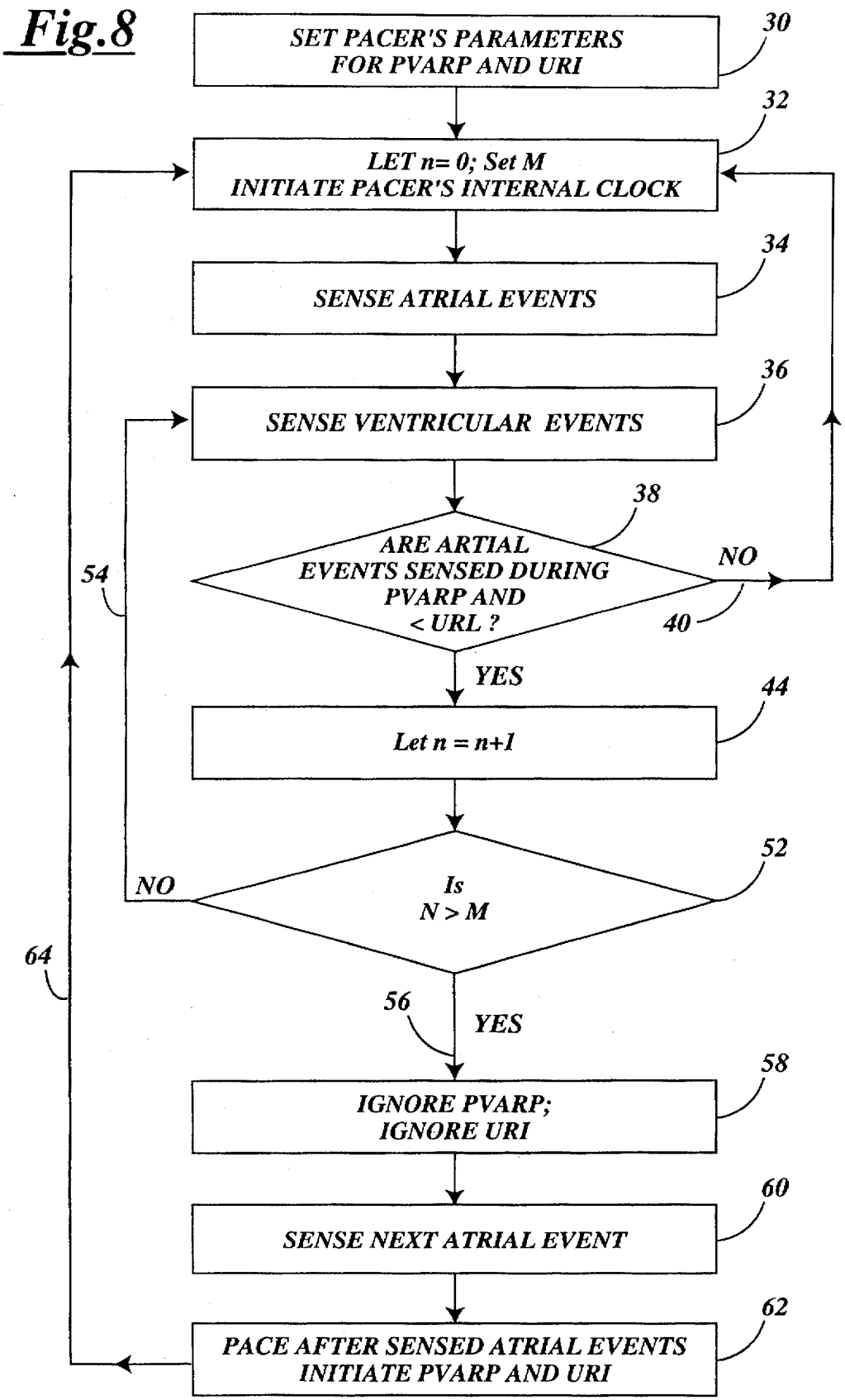
FIG. 8 is a flow diagram of the algorithm used to run the pacer's microprocessor-based controller to control the dual chamber pacing in accordance with the present invention.

Having generally described the method of breaking a PR+PVARP block, reference will now be made to the flow chart shown in FIG. 8 which further details the steps that the pacer programming implements in performing the PR+PVARP break algorithm. First the physician sets the pacer's parameters for PVARP and URI (see block 30) in accordance with the individual needs of the patient. The preferred pacemaker includes an internal clock which is initiated once the PVARP and URI are set. Additionally, a counter N is set to equal zero and a predetermined integer number M is programmed into the controller (see block 32). The atrial activity and ventricular activity are then sensed (see blocks 34 and 36) and signals associated with this activity are transmitted to the microprocessor-based controller included within the pacemaker. The pacemaker then determines whether any sensed atrial events have occurred during the PVARP (see decision block 38). If the atrial events were not sensed during PVARP, the pacing of the ventricle continues and the atrial and ventricular events are continued to be sensed (see loop 40). If the atrial events are sensed during PVARP, the counter N is increased by one (see block 44) and the pacer then determines whether the counter has been increased beyond a preset integer number M (see decision block 52) which is preprogrammed by the physician. In order to ensure that the detected atrial events are legitimate and not noise or retrograde conduction, the sinus rate should be less than the upper rate limit (URL). If the counter has not increased beyond the preset integer, the sensing of ventricular events continues (see loop 54). If the counter has exceeded the preset maximum M, the pacer shifts into a mode which ignores the pre-programmed PVARP and URI (see block 58). The pre-programmed PVARP and URI may be ignored over several cardiac cycles. Alternatively, only the PVARP may be shortened or ignored for a predetermined number of cardiac cycles. An additional alternative includes shortening or ignoring the PVARP until a rate of pacing the corresponding ventricle falls below the URL. After the predetermined number of cardiac cycles, the pacemaker continues sensing for atrial events at block 60, and as soon as an atrial event is sensed, the pacemaker then stimulates the ventricle after a preset AV-delay (see block 62) and reinitiates the PVARP and URI, thereby breaking the PR+PVARP block. The pacer then senses the atrial and ventricular events to determine when the next PR+PVARP block occurs (see loop 64).

This invention has been described herein in considerable detail in order to comply with the patent statutes and to provide those skilled in the art with the information needed to apply the novel principles and to construct and use such specialized components as are required. However, it is to be understood that the invention can be carded out by specifically different devices, and that various modifications, both as to the equipment details and operating procedures, can be accomplished without departing from the scope of the invention itself.

What is claimed is:

1. A method of pacing the heart of a congestive heart failure patient, said method utilizing a dual chamber cardiac pacer of the type having means for sensing atrial and ventricular events, a microprocessor-based controller coupled to the sensing means, and means controlled by the microprocessor-based controller for pacing the atrium and ventricles of a heart, the method comprising the steps of:

a) sensing atrial activity and transmitting a signal associated with said atrial activity to said microprocessor-based controller;
   b) sensing ventricular activity and transmitting a signal associated with said ventricular activity to said microprocessor-based controller;
   c) selecting a mode of the cardiac pacer to sense an atrial event and pace a corresponding ventricle after a preselected lapse of time following the sensed atrial event wherein a timing interval between sensing the atrial event and pacing the corresponding ventricle is controlled by said microprocessor based controller;
   d) establishing in the micro-processor based controller a post ventricular atrial refractory period (PVARP) and an upper rate interval (URI); then
   e) detecting an atrial event occurring during said PVARP; and
   f) then, resetting the timing interval of the microprocessor based controller after detecting an atrial event occurring during said PVARP.

2. The method as recited in claim 1, wherein the step of resetting the timing interval includes a breaking of a PR+PVARP block.

3. The method as recited in claim 2, wherein breaking of the PR+PVARP block is accomplished by blocking PVARP and URI until a succeeding atrial event is sensed.

4. The method as recited in claim 2, wherein the breaking of the PR+PVARP block is accomplished by shortening the PVARP for one cardiac cycle, wherein the cardiac cycle is determined by said microprocessor based controller having a means for determining the cardiac cycle.

5. The method as recited in claim 2, wherein the breaking of the PR+PVARP block is accomplished by shortening the PVARP for a selected number of cardiac cycles, wherein the cardiac cycles are determined by said microprocessor based controller having a means for determining cardiac cycles.

6. The method as recited in claim 2, wherein the breaking of the PR+PVARP block is accomplished by shortening the PVARP and URI for a selected number of cardiac cycles, wherein the cardiac cycles are determined by said microprocessor based controller having a means for determining cardiac cycles.

7. The method as recited in claim 2, further including the step of selecting an Upper Rate Limit (URL) of pacing by the cardiac pacer, wherein the breaking of the PR+PVARP block is accomplished by shortening the PVARP until a rate of pacing the corresponding ventricle falls below the URL.

8. The method as recited in claim 2, further including the step of selecting an Upper Rate Limit (URL) of pacing by the cardiac pacer, wherein the breaking of the Pr+PVARP block is accomplished by ignoring the PVARP until a rate of pacing the corresponding ventricle falls below the URL.

9. The method as recited in claim 1, wherein the step of detecting an atrial event is performed over a plurality of R—R intervals, wherein said microprocessor-based controller determines said R—R intervals from a means for determining the R—R intervals.

10. The method as recited in claim 1, wherein the step of resetting the timing interval of the microprocessor based controller includes the following steps:

i. blocking the post ventricular atrial refractory period;
   ii. blocking said URI setting;
   iii. after performing steps i. and ii., detecting signals associated with said atrial activity;
   iv. pacing the ventricle a predetermined amount of time after step iii.

11. The method as recited in claim 9, wherein the step of resetting the timing interval of the microprocessor-based controller includes the following steps:

i. blocking the post ventricular atrial refractory period;
   ii. blocking said URI setting;
   iii. after performing steps i. and ii., detecting signals associated with said atrial activity;
   iv. pacing the ventricle a predetermined amount of time after step iii.

* * * * *